United States Patent [19]

Wood

[11] Patent Number: 4,646,363
[45] Date of Patent: Mar. 3, 1987

[54] WELDERS HELMET

[76] Inventor: Timothy A. Wood, P.O. Box 465, Hermitage, Tenn. 37076

[21] Appl. No.: 814,956

[22] Filed: Dec. 31, 1985

Related U.S. Application Data

[63] Continuation of Ser. No. 678,851, Dec. 6, 1984, abandoned.

[51] Int. Cl.4 .......................... A42B 1/00; A61F 9/02
[52] U.S. Cl. ................................................. 2/8; 2/427
[58] Field of Search ...................................... 2/8, 427

[56] References Cited

U.S. PATENT DOCUMENTS

| | | | |
|---|---|---|---|
| 2,644,160 | 7/1953 | Jacobs | 2/8 |
| 3,868,727 | 3/1975 | Paschall | 2/8 |
| 4,109,132 | 8/1978 | Butoi | 2/8 X |
| 4,114,198 | 9/1978 | Sands | 2/8 |

Primary Examiner—Louis K. Rimrodt

[57] ABSTRACT

This invention relates to an improved construction for welders helmets (10); wherein a generally rectangular visor housing member (18) projects outwardly from the helmet face plate element (16), and contains a generally opaque visor element (13) disposed generally parallel to the face plate element (16), and a clear visor element (14) disposed generally perpendicular to the face plate element (16).

4 Claims, 3 Drawing Figures

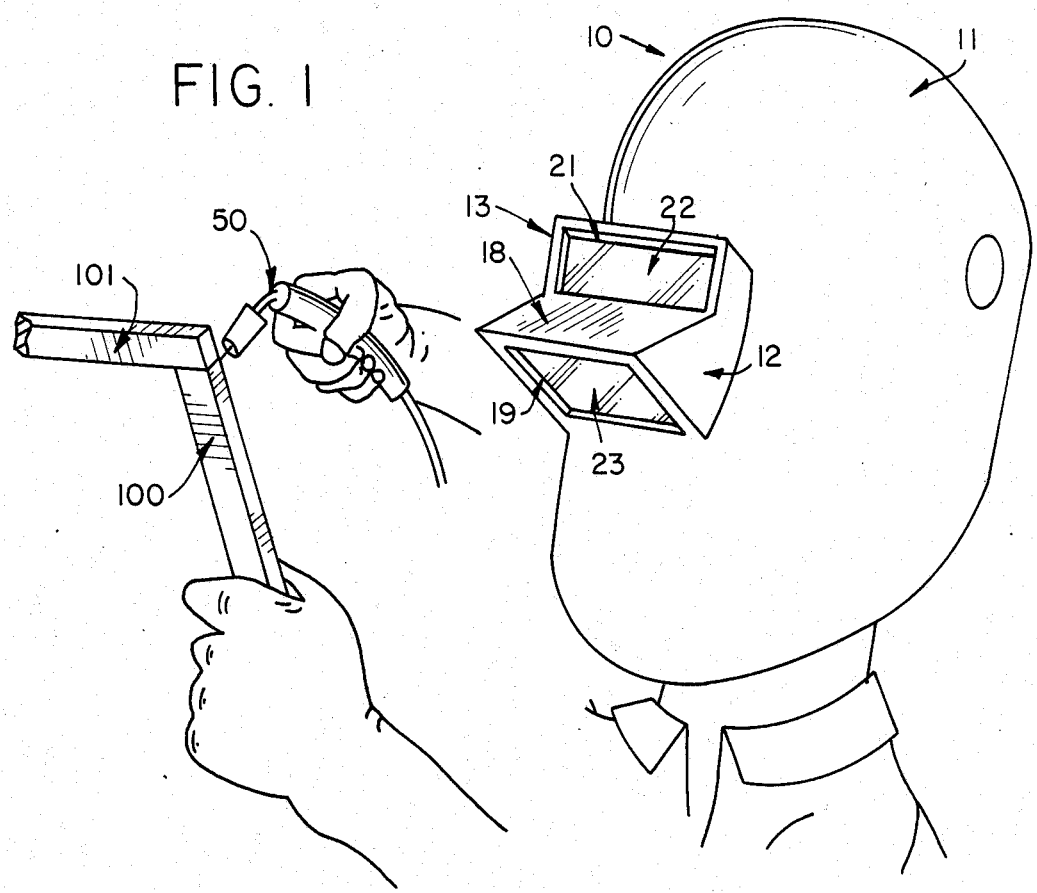
FIG. 1
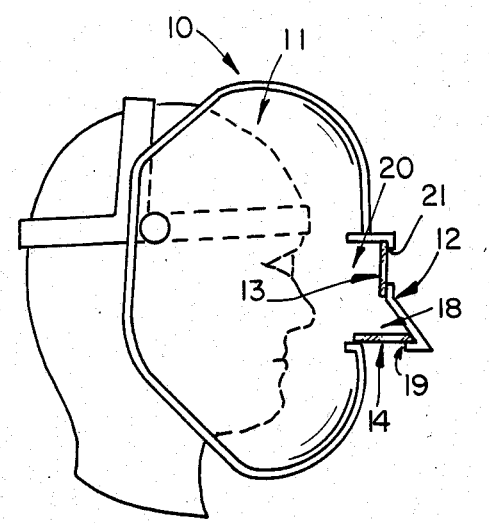
FIG. 2
FIG. 3

WELDERS HELMET

BACKGROUND OF THE INVENTION

This is a continuation application of U.S. patent application Ser. No. 678,851 filed Dec. 6, 1984 and entitled WELDERS HELMET now abandoned.

TECHNICAL FIELD

This invention relates generally to helmet constructions specifically designed for use in a welding environment.

The prior art is replete with various welder helmet constructions, as evidenced by the subject matter of the following U.S. Pat. Nos. 2,644,160; 3,868,727; 4,109,132; and 4,114,198.

As can be seen by reference to the above cited patents, most of the prior art helmet constructions provide both a clear and a relatively opaque visor element. The clear visor is normally disposed in a stationary relationship with respect to a pivoted opaque visor.

The aforementioned structural relationship allows the opaque visor to be pivoted away from the user's line of sight to provide an unobstructed view. While this type of a construction is adequate for its intended purpose; it does suffer in many practical respects during the actual welding process.

The Jacobs reference U.S. Pat. No. 2,644,160, disposes a narrow clear lens above the opaque lens so that the user can tilt his head to bring either of the lenses into play. However this construction does not allow the user to visually check the work disposed in front of and below the opaque visor.

The Butoi reference, U.S. Pat. No. 4,109,132, employs a pivoted opaque lens, that is either in its operative or inoperative position, depending upon its particular disposition. This arrangement only allows inspection of the work when the opaque visor is pivoted out of the users line of sight.

The Paschall reference, U.S. Pat. No. 3,868,727, discloses a clear, curved major element disposed on the forward portion of the major visor element. It should also be noted that this reference stresses that the lower edge of the minor visor element should be aligned with the tip of the users nose. While this arrangement allows the inspection of work disposed in front of and below the user's normal line of sight; it also suffers in that direct and/or reflected glare from the torch arc can be perceived by the user.

BRIEF DESCRIPTION OF THE INVENTION

The provision of the present invention overcomes virtually all of the objections, deficiencies and drawbacks found in the prior art welders' helmets. The present invention includes in general a helmet unit, a visor housing unit, an opaque visor element and a clear visor element.

The visor housing element projects outwardly from the front of the helmet unit, with the generally opaque visor element being disposed generally parallel to the face of the helmet unit in a generally vertical plane; and the clear visor element extending beyond the generally opaque visor element, and being disposed generally perpendicular to the face of the helmet unit in a generally horizontal plane.

This arrangement allows the user to accurately position members that are to be welded together by inspecting the position of the respective members through the transparent visor, and then commence the welding operation after the user tilts his or her head in order to bring the opaque visor into their line of sight.

BRIEF DESCRIPTION OF THE DRAWINGS

These and other objects, advantages, and novel features of the instant invention will become apparent from the description of the best mode for carrying out the invention which follows, when considered in conjunction with the accompanying drawings, wherein:

FIG. 1 is a perspective view of the present invention

FIG. 2 is a cross-sectional view of the present invention; and

FIG. 3 is a front elevational view of the present invention.

BEST MODE FOR CARRYING OUT THE INVENTION

As can be seen by reference to the drawings, and in particular to FIG. 1, the apparatus that forms the basis of the present invention is designated generally by the numeral (10). The apparatus (10) comprises generally a helmet unit (11), a visor housing unit (12), a generally opaque visor element (13), and a clear visor element (14). The aforementioned units and elements will now be described in seriatim fashion.

The helmet unit (11) includes generally a helmet member (15) comprising an elongated rigid curved face plate element (16) dimensioned and contoured to completely cover the user's face and neck. In the preferred embodiment, the face plate element (16) is fabricated from high impact plastic or the like; however, it should be appreciated that the invention is not intended to be limited to that material, and metal would be a suitable substitute for the purposes of the teachings of this invention.

The visor housing unit (12) comprises a generally rectangular visor housing member (17) projecting outwardly from the elongated rigid curved face plate element (16), and formed integrally therewith.

As can best be seen by reference to FIG. 2, the visor housing unit (12) is further provided with a lower portion (18) that projects outwardly with respect to the upper portion (20); and the lower portion (18) is further provided with a generally rectangular recess (19) dimensioned to receive the clear visor element (14). In addition, the upper portion (20) of the visor housing unit (12) is also provided with a generally rectangular recess (21), that is dimensioned to receive the generally opaque visor element (13).

As shown in the drawings, the forward face of the upper portion (20) of the housing unit (12) is disposed generally parallel to the forward portion of the face plate element (16); and the bottom surface of the lower portion (18) of the housing unit (12) is disposed generally perpendicular to the face plate element (16).

The generally opaque visor element (13) comprises an optical filter member (22), which is adapted to protect the user's eyes from the brilliant light generated by the welding torch arc, in a well recognized manner. The clear visor element (14) comprises a clear optical member (23) fabricated from tempered glass, clear plastic or the like.

It should be apparent at this point, that the particular construction of the visor elements (13) and (14) are not considered to form a part of this invention; however, the orientation of the visor elements and housing unit

(12) with respect to the helmet unit (11) are considered to form the crux of this invention.

Again referring to FIG. 2, it can be seen that the helmet apparatus (10) provides the user with a protective visor (13) directly in front of the user's eyes, and a clear visor (14) below the user's eye level. In addition, the totally opaque outwardly projecting lower portion (18) of the visor housing unit (12) precludes the direct impingement of the light emanating from the welding torch, upon the eyes of the user when the torch (50) is held in its normal working position. It is important to note that, the aforementioned structural relationship is particularly useful in situations wherein the user must maintain two workpieces (100), (101) in a specific relationship with one hand. While both hands are thus occupied, the user merely tilts his head upwardly to verify the position of the workpieces, and then resumes welding.

The aforementioned arrangement allows the user to leave the helmet apparatus (10) in its operative disposition throughout the welding process; and, will eliminate the requirement that the user adjust a structural component on the helmet apparatus, as was the case with most of the prior art devices. It should also be noted that the totally opaque visor housing unit provides a glare shield that completely surrounds the optical filter member (22) for added protection for the user's eyes.

Having thereby described the subject matter of this invention, it should be obvious at this point that many substitutions, modifications and variations of the invention are possible in light of the teachings contained herein. It is therefore to be understood, that the invention as taught and described, is only to be limited to the extent and breadth of the appended claims.

What I claim is:

1. An improved construction for a welder's helmet wherein the welder's helmet comprises an elongated rigid face plate element, and wherein the improvement consists of:
    a visor housing unit comprising a generally rectangular housing member projecting outwardly from the said rigid face plate element, wherein the housing member comprises an upper housing portion extending outwardly and disposed in a generally parallel plane with respect to said rigid face plate element, and a lower housing portion projecting outwardly with respect to said upper housing portion to form a glare shield, wherein the bottom surface of the lower portion is disposed generally perpendicular to the rigid face plate element.

2. The improved construction for a welders helmet as in claim 1; wherein, the improvement further comprises:
    a generally opaque visor element adapted to be received in the upper portion of the housing member and disposed in a plane generally parallel to said face plate element.

3. The improved construction for a welder's helmet as in claim 2; wherein, the improvement further comprises:
    a clear visor element disposed within the lower housing portion.

4. An improved construction for a welder's helmet wherein the welder's helmet comprises an elongated rigid face plate element, and wherein the improvement consists of:
    a visor housing unit comprising a generally rectangular housing member projecting outwardly from the said rigid face plate element, wherein the housing member comprises an upper housing portion extending outwardly and disposed in a generally parallel plane with respect to said rigid face plate element, and a lower housing portion projecting outwardly with respect to said upper housing portion, wherein the bottom surface of the lower housing portion, wherein the bottom surface of the lower housing portion is disposed generally perpendicular to the rigid face plate element;
    a generally opaque visor element adapted to be received in the upper portion of the housing member, and disposed in a plane generally parallel to said face plate element; and,
    a clear visor element forming a portion of the bottom surface of the lower hanging portion, whereby said clear visor element is disposed generally perpendicular to both the generally opaque visor element and the said face plate element.

* * * * *